(12) United States Patent
Debruyne et al.

(10) Patent No.: US 8,515,560 B2
(45) Date of Patent: Aug. 20, 2013

(54) MEDICAL IMPLANT DRUG DELIVERY DEVICE

(75) Inventors: Kristine Debruyne, Mechelen (BE); Dirk Fiedler, Lane Cove (AU); Thomas Kaiser, Mechelen (BE); Ben Kloeck, Mechelen (BE); Dusan Milojevic, Westleigh (AU); John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 1410 days.

(21) Appl. No.: 10/536,714

(22) PCT Filed: Nov. 28, 2003
(Under 37 CFR 1.47)

(86) PCT No.: PCT/AU03/01584
§ 371 (c)(1),
(2), (4) Date: Aug. 9, 2006

(87) PCT Pub. No.: WO2004/050056
PCT Pub. Date: Jun. 17, 2004

(65) Prior Publication Data
US 2006/0287689 A1    Dec. 21, 2006

(30) Foreign Application Priority Data

Nov. 29, 2002 (AU) ............... 2002952995
Nov. 29, 2002 (AU) ............... 2002952997
Nov. 29, 2002 (AU) ............... 2002952998

(51) Int. Cl.
*A61N 1/05* (2006.01)

(52) U.S. Cl.
USPC ............... 607/137; 607/57; 607/120

(58) Field of Classification Search
USPC ............... 607/57, 120, 137
See application file for complete search history.

(56) References Cited

U.S. PATENT DOCUMENTS

| 4,306,563 A | 12/1981 | Iwatschenko |
| 4,351,337 A | 9/1982 | Sidman |
| 4,357,497 A | 11/1982 | Hochmair et al. |
| 4,532,930 A | 8/1985 | Crosby et al. |
| 4,784,161 A * | 11/1988 | Skalsky et al. ............... 607/116 |
| 4,819,662 A | 4/1989 | Heil et al. |
| 4,994,069 A | 2/1991 | Ritchart et al. |
| 5,066,278 A | 11/1991 | Hirschberg et al. |
| 5,458,631 A | 10/1995 | Xavier |

(Continued)

FOREIGN PATENT DOCUMENTS

| DE | 100 320 000 A1 | 1/2001 |
| EP | 0007157 | 1/1980 |

(Continued)

OTHER PUBLICATIONS http://www.merriam-webster.com/dictionary/lumen, accessed 3/38/2011.*

(Continued)

*Primary Examiner* — Joseph Stoklosa
(74) *Attorney, Agent, or Firm* — Kilpatrick, Townsend & Stockton, LLP.

(57) ABSTRACT

Devices for the delivery of a bioactive substance to a cochlea and methods of delivery thereof. The devices include means to allow the release of the bioactive substance within a cochlea.

13 Claims, 9 Drawing Sheets

(56) References Cited

U.S. PATENT DOCUMENTS

| | | | |
|---|---|---|---|
| 5,474,542 | A | 12/1995 | Gandi et al. |
| 5,531,780 | A | 7/1996 | Vachon |
| 5,554,114 | A | 9/1996 | Wallace et al. |
| 5,653,742 | A | 8/1997 | Parker et al. |
| 5,697,951 | A | 12/1997 | Harpstead et al. |
| 5,755,474 | A | 5/1998 | Slomski |
| 5,929,041 | A | 7/1999 | Magal |
| 5,975,085 | A | 11/1999 | Rise |
| 6,038,482 | A | 3/2000 | Vachon |
| 6,038,484 | A | 3/2000 | Kuzma |
| 6,078,841 | A | 6/2000 | Kuzma |
| 6,125,302 | A | 9/2000 | Kuzma |
| 6,163,729 | A | 12/2000 | Kuzma |
| 6,259,951 | B1 | 7/2001 | Kuzma et al. |
| 6,304,787 | B1 | 10/2001 | Kuzma et al. |
| 6,309,410 | B1 | 10/2001 | Kuzma et al. |
| 6,321,125 | B1 * | 11/2001 | Kuzma ............... 607/137 |
| 6,398,758 | B1 | 6/2002 | Jacobsen et al. |
| 6,421,569 | B1 | 7/2002 | Treaba et al. |
| 6,936,040 | B2 * | 8/2005 | Kramm et al. ......... 604/508 |
| 7,044,942 | B2 * | 5/2006 | Jolly et al. ........... 604/891.1 |
| 7,272,449 | B2 | 9/2007 | Dadd et al. |
| 7,571,012 | B2 | 8/2009 | Gibson |
| 2002/0077685 | A1 | 6/2002 | Sundquist et al. |
| 2003/0097121 | A1 | 5/2003 | Jolly et al. |

FOREIGN PATENT DOCUMENTS

| | | |
|---|---|---|
| EP | 0706807 | 4/1996 |
| JP | 55000190 | 1/1980 |
| JP | 08229137 | 9/1996 |
| JP | 09508054 | 8/1997 |
| JP | 11514252 | 12/1999 |
| WO | WO-9615665 | 5/1996 |
| WO | WO 97/10784 | 3/1997 |
| WO | WO 99/00067 | 1/1999 |
| WO | WO-9911321 | 3/1999 |
| WO | WO 99/55360 A1 | 11/1999 |
| WO | WO/00/57949 | 3/2000 |
| WO | WO-0056399 | 9/2000 |
| WO | WO 00/71063 | 11/2000 |
| WO | WO-0071063 | 11/2000 |
| WO | WO/01/41674 | 6/2001 |
| WO | WO-0197908 | 12/2001 |
| WO | WO-0224064 | 3/2002 |
| WO | WO 02/32498 A1 | 4/2002 |
| WO | WO 02/4166 | 5/2002 |
| WO | WO 02/41666 | 5/2002 |
| WO | WO 02/41666 A1 | 5/2002 |
| WO | WO/02/083234 | 10/2002 |
| WO | WO-02087681 | 11/2002 |
| WO | WO/03/049658 | 6/2003 |
| WO | WO 03/072193 | 9/2003 |

OTHER PUBLICATIONS

Altschuler, et al., "Rescue and Regrowth of Sensory Nerves Following Deafferentation by Neurotrophic Factors," Nov. 28, 1999, Annals New York Academy of Sciences. 884:305-11.

Supplementary European Search Report for EP 01 99 4538, dated May 27, 2005.

International Preliminary Examination Report for PCT/AU01/01479.

Supplementary Partial European Search Report for EP 03 70 2212 dated Jun. 23, 2006.

International Search Report, PCT/AU01/01479 dated Dec. 3, 2001.

Written Opinion, PCT/AU01/01479 dated Jan. 28, 2002.

AU 2002223270, "First Examination Report", Aug. 17, 2005.

AU 2003283124, "First Examination Report," dated Jun. 13, 2008.

AT $2^{nd}$ Office Action and English Translation for PCT/AU2003/001584, Dated Mar. 20, 2007.

AU 2007202203, "Australian Examination Report of application No. AU 2007202203, dated Oct. 22, 2008".

EP 01994538, "Examination Report", Apr. 20, 2007.

CA Office Action for Application No. 2,428,542 dated May 15, 2009.

JP 2002-543261, "Notice of Reason(s) for Rejection issued Jan. 9, 2007 in Japanese Application No. 2002-543261".

PCT/AU2003/001584, "International Preliminary Examination Report", Mar. 15, 2005.

International Search Report for PCT/AU2003/01584, mailed Apr. 2, 2004.

* cited by examiner

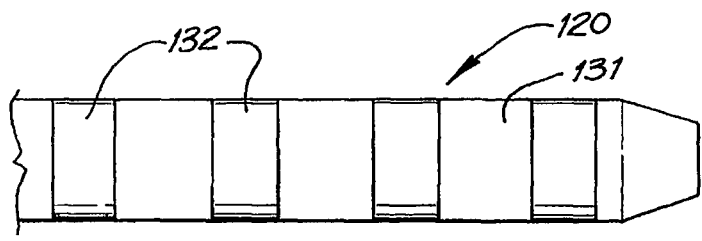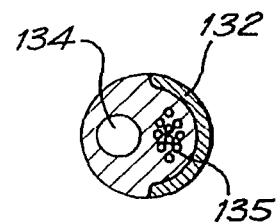
FIG. 10a
PRIOR ART
FIG. 10b
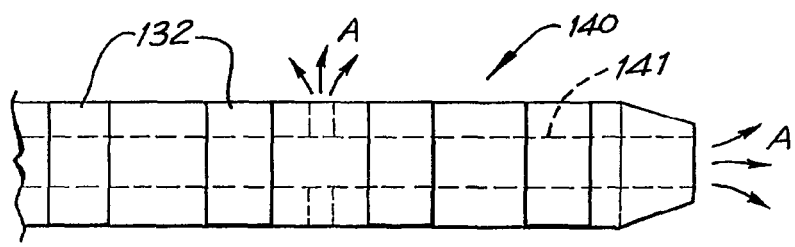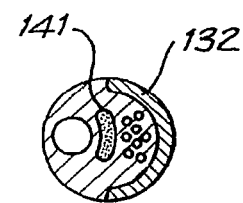
FIG. 11
FIG. 11a
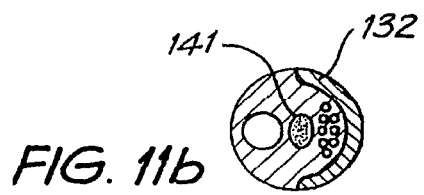
FIG. 11b
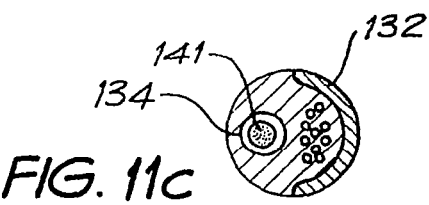
FIG. 11c

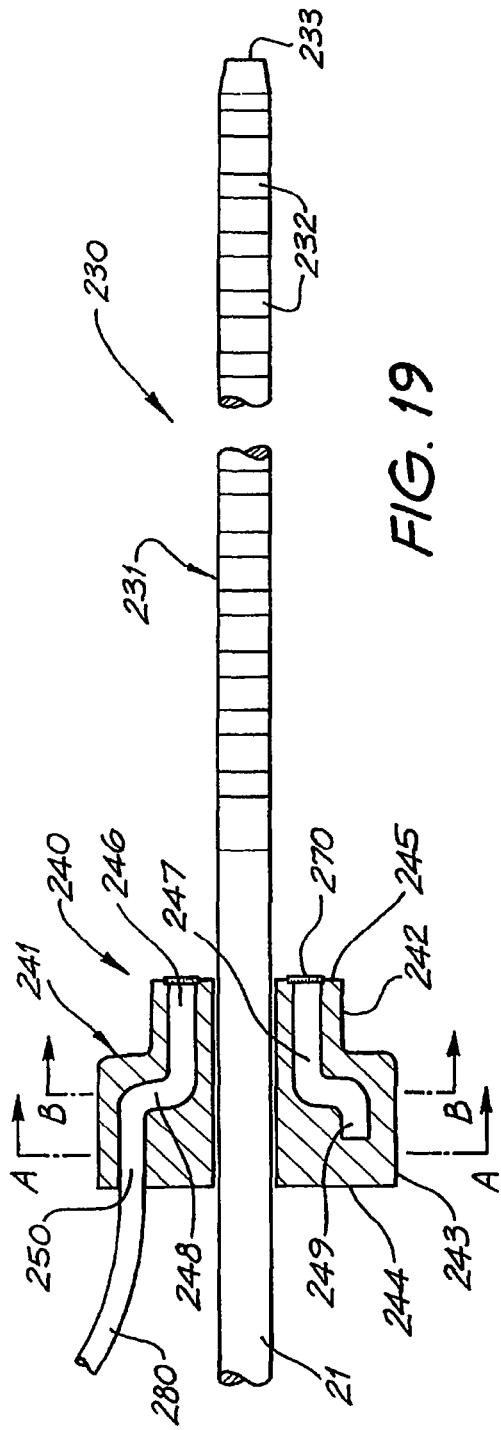
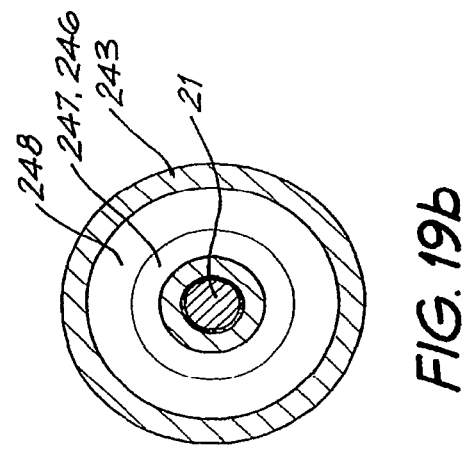
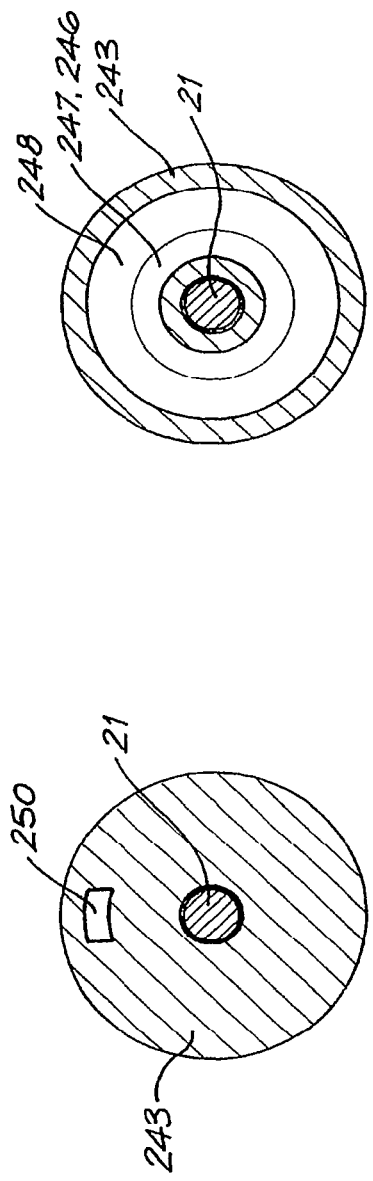

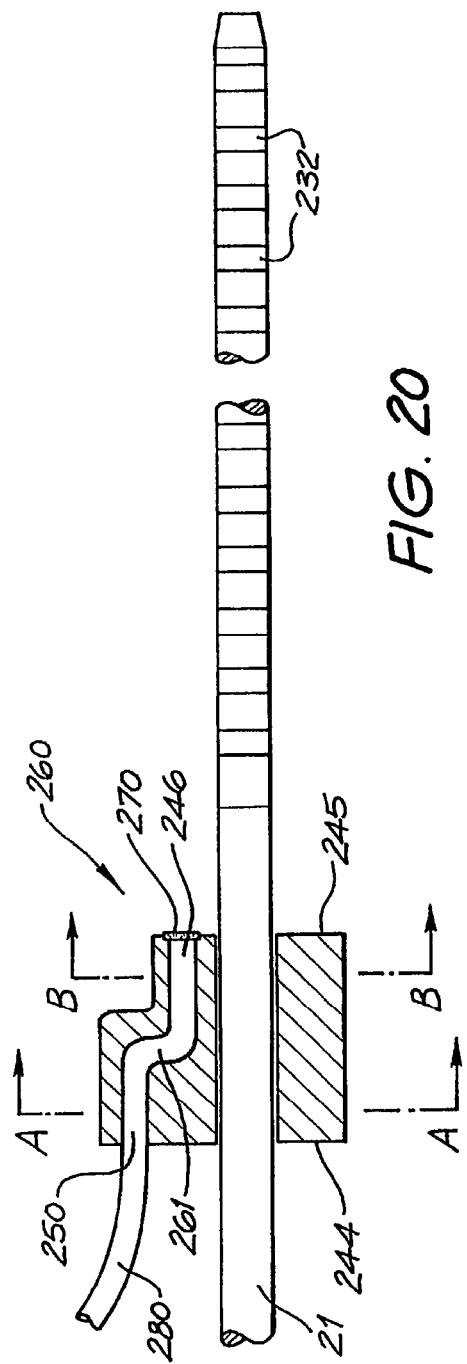

MEDICAL IMPLANT DRUG DELIVERY DEVICE

CROSS-REFERENCE TO RELATED APPLICATIONS

This application claims the priority of and is a national stage application of PCT Application No. PCT/AU2003/001584, entitled, "Cochlear Implant Drug Delivery Device," filed on Nov. 28, 2003, which claims the priority of Australian Patent No. 200252995, Australian Patent No. 2002952997, and Australian Patent No. 2002952998, that were each filed on Nov. 29, 2002. The entire disclosure and contents of the above applications are hereby incorporated by reference.

FIELD OF THE INVENTION

The present invention relates to an implantable device and, in particular, to an implantable device for use in delivering pharmaceuticals to a cochlea following implantation of an electrode assembly.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that hearing implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Hearing implant systems have typically consisted of two key components, namely an external component commonly referred to as a processor unit, and an implanted internal component commonly referred to as a receiver/stimulator unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted receiver/stimulator unit situated within a recess of the temporal bone of the implantee. This transcutaneous transmission occurs through use of an inductive coupling provided between the external antenna transmitter coil which is positioned to communicate with an implanted antenna receiver coil provided with the receiver/stimulator unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit typically includes the antenna receiver coil that receives the coded signal and power from the external processor component, and a stimulator that processes the coded signal and outputs a stimulation signal through a lead to an intracochlea electrode assembly which applies the electrical stimulation directly to the auditory nerve producing a hearing sensation corresponding to the original detected sound.

The electrode assembly is typically implanted through a cochleostomy formed in the cochlea and comprises an array of electrodes, with each electrode being arranged and constructed to deliver a cochlea stimulating signal within a preselected frequency range to an appropriate cochlea region. The electrical currents and electric fields from each electrode stimulate the cilia disposed on the modiolus of the cochlea. Several electrodes may be active simultaneously.

There have been a number of proposals for delivering bioactive substances to the cochlea that are beneficial in promoting acceptance of the electrode assembly within the cochlea and/or assisting in the function of the auditory nerve. One such proposal is described in the present applicant's International Application No PCT/AU01/01479 which describes use of a lumen within the electrode assembly that delivers bioactive substances directly within the cochlea following implantation of the assembly.

The present invention provides an alternative system for delivering beneficial bioactive substances to the region of the cochlea of a patient and particularly an implantee of a hearing implant.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Generally, the present invention provides a device that is adapted to assist in the delivery of pharmaceutical treatment to surrounding tissue following the insertion and positioning of an electrode assembly. Typically, the electrode assembly is positioned in order to apply electrical stimulation to a target region of tissue via dedicated electrical stimulating electrodes. The present invention is applicable to all types of tissue stimulating devices such as hearing implants, deep brain implants, spinal cord implants and any other implantable devices that treat neurosensory or motorsensory loss or dysfunction.

It is a preferred feature of the present invention to provide a device that is adapted to assist the cochlea in its recovery from trauma following the insertion of an electrode assembly therein. The present invention is equally applicable to conventional straight electrode assemblies and electrode assemblies which are designed to conform with the inner wall of the cochlea.

According to a first aspect, the present invention is a drug delivery device comprising:

a resiliently flexible elongate member having a proximal end and a distal end for implantation within a body;

wherein at least a portion of said elongate member is comprised of a porous biocompatible material, at least some of the pores having at least one bioactive substance disposed therein prior to implantation, said at least one bioactive substance being adapted to migrate from the pores following implantation of the member.

In this aspect, the resiliently flexible elongated member can form part of an implantable tissue-stimulating device having at least one electrode mounted thereon.

In another embodiment of this aspect, the drug delivery device can be separate to a tissue stimulating device but which acts in conjunction with said tissue stimulating device.

According to a second aspect, the present invention is an implantable tissue-stimulating device comprising:

a resiliently flexible elongate member having a proximal end and a distal end and at least one electrode mounted thereon between said proximal and distal ends for delivering electrical stimulation;

wherein at least a portion of said elongate member is comprised of a porous biocompatible material, at least some of the pores having at least one bioactive substance disposed therein prior to implantation, said at least one bioactive substance being adapted to migrate from the pores following implantation of the member.

In a preferred embodiment of this invention, the device is a cochlear™ implant electrode assembly, with the elongate member adapted to be inserted through a cochleostomy formed in the cochlea and positioned therein.

In one embodiment, the elongate member can be comprised of one or more porous portions. In one embodiment, the porous portions can comprise the same material as the remainder of the elongate member but having a plurality of pores disposed therethrough. In one embodiment, the porous portions can comprise the same material as the remainder of the elongate member but which has undergone a processing step to render the portions foraminous. In another embodiment, a majority, or the entire body, of the elongate member can be porous.

In one embodiment of this aspect, the elongate member can be formed from a silicone material.

In yet another embodiment, the porous portions can be formed from a different material to that of the remainder of the elongate member. In one embodiment, the porous portions can act as electrodes for delivering electrical stimulation at the site of implantation of the elongate member. In this embodiment, the electrodes can be formed from a suitable porous metallic material. The metallic material can be a suitable porous platinum. In another embodiment, the porous portions can be formed from a suitable porous metallic material, such as a porous platinum, mounted in the elongate member but where the portions are not adapted to deliver electrical stimulation.

In one embodiment, all of the electrodes mounted to the elongate member can be formed from the suitable metallic material, such as a porous platinum. In another embodiment, only some of the electrodes can be porous, with some of the electrodes being formed from a suitable relatively non-porous metallic material, such as platinum as is discussed in further detail below.

In a still further embodiment, the device can further comprise a sheath comprised at least in part of a porous material disposed over at least a portion of the elongate member. In a preferred embodiment, a majority of and, more preferably, the entire elongate member can be sheathed in the porous material. Still further, at least a majority and, more preferably, the entire sheath is formed of a porous material.

According to a third aspect, the present invention is an implantable tissue-stimulating device comprising:

a resiliently flexible elongate member having a proximal end and a distal end and at least one electrode mounted thereon between said proximal and distal ends for delivering electrical stimulation; and a sheath comprised at least in part of a porous material disposed over at least a portion of the elongate member;

wherein at least some of the pores of the sheath have at least one bioactive substance disposed therein prior to implantation, said at least one bioactive substance being adapted to migrate from the pores following implantation of the member.

According to a fourth aspect, the present invention is an implantable tissue-stimulating device comprising:

a resiliently flexible elongate member having a proximal end and a distal end; and at least one electrode mounted on the elongate member between said proximal end and said distal end for delivering electrical stimulation;

wherein at least one of said at least one electrode is comprised of a porous biocompatible material, at least some of the pores having at least one bioactive substance disposed therein prior to implantation, said at least one bioactive substance being adapted to migrate from the pores following implantation of the member.

In this aspect, said at least one electrode can be formed from a suitable porous electrically conductive material. The electrically conductive material can be a suitable porous metallic material. The metallic material can be a suitable porous platinum. In one embodiment of this aspect, all of the electrodes mounted to the elongate member can be formed from the suitable electrically conductive material, such as a porous platinum. In another embodiment, only some of the electrodes can be porous, with some of the electrodes being formed from a suitable relatively non-porous metallic material, such as platinum.

In each of the above aspects, each pore of the porous portion can be an individual pore within the portion, making no interconnection with another pore in the portion. In this embodiment, at least some or each of the pores can be aligned and/or equally spaced with respect to each other. In another embodiment, some of the pores can be interconnected with at least some other pores within the porous portion. In yet another embodiment, the pores can be arranged in a random order with some of the pores being interconnected with at least some of the other pores and some of the pores not interconnected with any of the other pores.

In a further embodiment, at least some of the pores or each pore of the porous portion can be at least substantially uniform in cross-sectional shape relative to each other. In another embodiment, the pores can vary in cross-sectional shape from one to at least some of the others.

In a still further embodiment, at least some of the pores or each pore of the porous portion can be substantially uniform in diameter. In another embodiment, the pores can vary in diameter from one to at least some of the others.

In yet another embodiment, at least some of the pores or each pore of the porous portion can be of a substantially constant diameter along its length. In another embodiment, at least some of the pores or each pore can vary in diameter along its length.

In a still further embodiment, at least some of the pores or each pore of the porous portion can have a substantially uniform cross-sectional shape along its length. In another embodiment, at least some of the pores or each pore can vary in cross-sectional shape along its length.

In yet another embodiment, at least some of the pores or each pore of the porous portion can be of a substantially constant length. In another embodiment, at least some of the pores or each pore can vary in length relative to at least some of the others in that portion. In one embodiment, at least some of the pores can have relatively extended lengths compared to other pores in that portion.

In still another embodiment, at least some of the pores or each pore of the porous portion can be at least substantially linear. In another embodiment, at least some of the pores or each pore of the porous portion can be non-linear.

In a still further embodiment, at least some of the porous portions or each porous portion can have substantially the same number of pores per unit area. In another embodiment, at least some of the porous portions or each porous portion can have differing number of pores per unit area relative to that of at least some of the other porous portions.

In yet another embodiment, at least some of the pores in one, some or each of the porous portions can have relatively smooth internal walls. In another embodiment, at least some of the pores in one, some or each of the porous portions can have rippled internal walls. The ripples can have a suitably small dimension to preferably at least substantially prevent wetting of the cavities thereby minimising friction between the bioactive substance and the walls.

In one embodiment, the nature of the porosity between separate porous portions of the device may be the same or vary from one to at least some or all of the other portions. For example, the dimension of the pores of a porous portion relatively close to the distal end of the elongate member may be different to the dimensions of the pores of a porous portion that is relatively close to the proximal end of the elongate member. In this embodiment, the portion relatively closer to the distal end can have pores having a diameter and/or length greater than the pores of the porous portion relatively closer to the proximal end of the elongate member. In another embodiment, the relative porosity of different portions can be essentially random.

In a further embodiment, at least some of the pores of the porous portion can be preferably adapted to be at least substantially closed when the elongate member is at least substantially straight thereby preventing migration of any bioactive substance held within said at least some pores from these pores. On adopting a curved configuration, said at least some pores can be adapted to at least partially open allowing migration of the bioactive substance therefrom.

In one embodiment, the bioactive substances can be free to simply migrate from the pores of the porous portions following implantation of the device. In another embodiment, the bioactive substance can be dispersed in a fluid and particularly an ionic fluid that is preferably caused to migrate from the pores on application of a suitable electrical field thereto. In another embodiment, the bioactive substance can be dispersed in an ionic solution that is allowed to diffuse from the pores and/or be expelled therefrom under application of a suitable electric field.

In a fifth aspect, the present invention is a method of delivering at least one bioactive substance to a desired site of action within a cochlea using a device as defined in the above aspects and embodiments thereof, the method comprising the steps of:

forming a cochleostomy;
inserting the elongate member through the cochleostomy;
allowing or causing the bioactive substance to migrate from the elongate member into the cochlea.

The pores of the device may be at least partially filled by dipping the elongate member in the bioactive substance for a suitable time period. This step can be performed immediately after manufacture of the elongate member. In another embodiment, the step can be performed just prior to implantation of the member into the implantee.

According to a sixth aspect, the present invention is a drug delivery device comprising:

a resiliently flexible elongate member having a proximal end and a distal end for implantation within a body;
wherein at least a portion of said elongate member is comprised of a biocompatible polymeric material, having at least one bioactive substance impregnated therein, said at least one bioactive substance being adapted to diffuse from the polymeric material following implantation of the member.

In this aspect, the resiliently flexible elongated member can form part of an implantable tissue-stimulating device having at least one electrode mounted thereon.

In another embodiment of this aspect, the drug delivery device can be separate to a tissue stimulating device but which acts in conjunction with said tissue stimulating device According to a seventh aspect, the present invention is an implantable tissue-stimulating device comprising:

a resiliently flexible elongate member having a proximal end and a distal end and at least one electrode mounted thereon between said proximal and distal ends for delivering electrical stimulation;
wherein at least one portion of said elongate member is comprised of a biocompatible polymeric material having at least one bioactive substance impregnated therein prior to implantation, said at least one bioactive substance being adapted to diffuse from the polymeric material following implantation of the member.

In a preferred embodiment of this invention, the device is a cochlear implant electrode assembly, with the elongate member adapted to be inserted through a cochleostomy formed in the cochlea and positioned therein.

In another embodiment, said portion of the biocompatible polymeric material is fully or partially encapsulated inside the material comprising the elongate member. In another embodiment, it can comprise a coating or be relatively near the surface of the elongate member. In one embodiment, the portion extends into the elongate member from at or adjacent the distal end. In this and other embodiments, the portion can extend for a majority of the length of the elongate member. In another embodiment, the portion extends the entire length of the elongate member between the proximal end and the distal end thereof. In this embodiment, said portion can be of constant diameter along its length. In another embodiment, said portion can vary in diameter along its length. For example, the diameter of said portion can decrease from the proximal end towards the distal end of the elongate member.

In a still further embodiment, one or more openings can be provided in the elongate member to allow bioactive substances in said portion to diffuse from said portion and exit the elongate member. An opening can be provided at the proximal end and/or the distal end of the elongate member. In another embodiment, there can be one or more openings between the proximal end and the distal end. Where there is more than one opening, the openings can be regularly or irregularly spaced along the elongate member.

In a still further embodiment, said at least one portion can be disposed in the outer face of the elongate member. In one embodiment, said portion can comprise a ring member disposed in the outer face of the elongate member. In another embodiment, said portion can comprise a portion of a ring member, such as a half-ring. In another embodiment, a number of portions can be disposed along the locus of a ring formed in the outer surface of the elongate member. In a still further embodiment, there can be provided a plurality of rings or ring portions, such as half rings, in the outer surface of the elongate member. In these embodiments, the one or more portions can be at least substantially flush with the outer surface of the elongate member. In another embodiment, the one or more portions can stand proud of or be recessed in the elongate member.

In a still further embodiment, the portions can be disposed adjacent said one or more electrodes in the elongate member. In another embodiment, at least one of said portions can be disposed between each of the electrodes mounted on the elongate member.

In a still further embodiment, one of said portions can be disposed around one, each of some or each of all the electrodes mounted in the elongate member. Where the electrode comprises a ring or ring portion, the portion can comprise an annular or part-annular member that surrounds the electrode.

In yet a further embodiment, the electrode can be disposed around a portion of said biocompatible polymeric material. Where a plurality of electrodes are mounted on the elongate member, some or each of the electrodes can be disposed around separate portions of said biocompatible polymeric material.

In one embodiment, the biocompatible polymeric material is non-degradable and the bioactive substance may be released by gradual diffusion through the polymeric material. Initially, bioactive substance molecules closest to the surface of the polymeric material are released. As release continues, molecules must travel a greater distance to reach the surface and thus the time required for the release increases. Accordingly, the amount of bioactive substance released may decrease with time.

According to an eighth aspect, the present invention is a drug delivery device comprising:

a resiliently flexible elongate member having a proximal end and a distal end for implantation within the body;

wherein at least a portion of said elongate member is comprised of a biodegradable, biocompatible polymeric material having at least one bioactive substance impregnated therein, said at least one bioactive being adapted to be released upon at least partial degradation of said polymeric material.

According to a ninth aspect, the present invention is an implantable tissue-stimulating device comprising:

a resiliently flexible elongate member having a proximal end and a distal end and at least one electrode mounted thereon between said proximal and distal ends for delivering electrical stimulation;

wherein at least one portion of said elongate member is comprised of a biodegradable, biocompatible polymeric material having at least one bioactive substance impregnated therein, said at least one bioactive being adapted to be released upon at least partial degradation of said polymeric material.

The breakdown of the biodegradable polymeric material may occur via gradual hydrolysis of the polymeric material or via biodegradation of the polymer structure caused by chemical or enzymatic processes.

Examples of suitable biodegradable polymers include poly(acrylic acid), poly(ethylene glycol), poly(vinylpyrrolidone), poly(hydroxybutyrate), poly(lactide-co-glycolide), polyanhydrides.

According to a tenth aspect, the present invention is a method of delivering at least one bioactive substance to a desired site of action within a cochlea using a device as defined in the sixth and seventh aspects, the method comprising the steps of:

forming a cochleostomy;

inserting the elongate member through the cochleostomy;

allowing the bioactive substance to diffuse from the elongate member into the cochlea.

According to an eleventh aspect, the present invention is a method of delivering at least one bioactive substance to a desired site of action within a cochlea using a device as defined in the eighth and ninth aspects, the method comprising the steps of:

forming a cochleostomy;

inserting the elongate member through the cochleostomy;

allowing or causing at least a portion of the biodegradable, biocompatible polymeric material to at least partially degrade allowing release of the bioactive substance therefrom.

According to a twelfth aspect, the present invention is an implantable tissue-stimulating device comprising:

a lead;

a resiliently flexible elongate member extending from the lead and having a proximal end and a distal end and at least one electrode mounted thereon between said proximal and distal ends for delivering electrical stimulation; and a bioactive substance delivery means adapted to deliver at least one bioactive substance to the implantee at a location spaced from the distal end of the member during and/or following implantation of the device;

wherein the substance delivery means comprises a body defining a chamber and an outlet in communication with the chamber through which bioactive substance can exit the body and further wherein the body is relatively slidably mounted to the lead of the device.

In a preferred embodiment of this invention, the device is a cochlear implant electrode assembly, with the elongate member adapted to be inserted through a cochleostomy formed in the cochlea and positioned therein. In this embodiment, the outlet of the substance delivery means is preferably positionable outside and adjacent the cochleostomy site. In this embodiment, the body is preferably relatively slidable along the lead until it reaches a location along the lead that results in it being positioned just outside the cochleostomy following implantation.

In a preferred embodiment, the lead can be provided with a stop means that prevents the body of the substance delivery means from being moved relatively past the stop means and onto the elongate member. In another embodiment, the stop means can comprise a stop member that, once engaged with the body, prevents subsequent slidable movement of the collar relative to the lead in either direction.

In a preferred embodiment, the elongate member is formed from a suitable biocompatible material.

In a further embodiment, the body of the substance delivery means comprises an annular member that is positioned around the lead of the stimulating device. The body preferably has an outer surface. In another embodiment, the annular member can comprise a cylindrical collar member. In this embodiment, the body preferably has a longitudinal axis. In one embodiment, the body can be symmetrical or non-symmetrical about the longitudinal axis.

In another embodiment, the body can comprise a portion of a ring, such as a half-pipe.

The annular member can comprise a first portion and a second portion, the second portion having an outer diameter less than that of the first diameter. In one embodiment, both the first portion and the second portion can be cylindrical. In this case, the outer surface preferably has a step between the first and second portion. The outer diameter of the first portion can be about twice that of the elongate member. In one embodiment, the first portion can have an outer diameter of about 1.2 mm.

In yet a further embodiment, the body can have a proximal end and a distal end. The proximal and distal ends can be at least substantially parallel or parallel.

In a further embodiment, the outlet of the body can be positioned in the distal end of the body. In a still further embodiment, the body can have an inlet in the proximal end of the body. The inlet and outlet are preferably in communication, such as fluid communication, with each other.

In a still further embodiment, the outlet of the body can comprise an annular opening in the distal end of the body. The chamber within the body can extend back into the body from the outlet. Where the outlet is an annular opening, the chamber can also be annular in form and so comprise a cylindrical chamber having an outer and inner surface and extending back into the body from the outlet.

In a still further embodiment, the annular chamber has a region where the outer wall of the chamber moves away from the longitudinal axis or the lead passing through the body as the chamber extends back into the body from the outlet. In this embodiment, the inner wall of the chamber can also move away from the longitudinal axis or the lead in said region. In one embodiment, the chamber can have a frusto-conical portion. In yet a further embodiment, the chamber can comprise a portion distal the outlet that is also cylindrical in form. In this embodiment, the inlet preferably comprises a pipe extending from the proximal end of the body into the chamber. The inlet is preferably adjacent the outer wall of the body.

In a still further embodiment, the chamber can comprise a pipe extending from the proximal end to the distal end of the body. The pipe is preferably non-linear. In one embodiment, the inlet can be positioned at least partially further outwardly from the longitudinal axis of the body relative to the outlet. In this embodiment, the collar can be non-symmetrical about its longitudinal axis.

The distal end of the elongate member is preferably firstly inserted into the cochleostomy of the implantee during placement of the implant.

The chamber in the body can act as a reservoir for a bioactive substance. In one embodiment, the bioactive substance in the reservoir can leach from the chamber into the implantee. In one embodiment, the outlet can have a semi-permeable membrane. The membrane preferably allows the bioactive substance to leach from the chamber during and/or following implantation to the desired site of action for the bioactive substance.

Where the bioactive substance is carried in or comprises a fluid, the semi-permeable membrane preferably allows the fluid to leach or diffuse therethrough.

The membrane can act as a valve means that allows fluid to exit the chamber but prevents, or at least substantially prevents, fluid flow from external the chamber back into the chamber within the body.

In a further embodiment, the inlet of the body can be in communication, such as fluid communication, with an additional reservoir for the bioactive substance that is external or internal the body of the implantee. A catheter can extend from the inlet to the additional reservoir. A pump, such as an osmotic pump, can transfer the bioactive substance from the additional reservoir into the chamber of the body for subsequent delivery to the appropriate site of action.

It is also envisaged that the bioactive substance can be captured in the form of a solid or semi-solid pellet. In one embodiment, the pellet can be formed by impregnating the bioactive substance in a ceramic or a polymer pellet that has a predetermined rate of release of the bioactive substance. This solid pellet can then be stored in the chamber or in an external reservoir connectable to the chamber.

The device of this aspect may be adapted to only provide delivery of a bioactive substance to the preferred site for a particular period following implantation. This period may comprise any period of time from a few hours or days to a few weeks or even months. In another embodiment, the device can be used as a means of delivery of bioactive substances to the implantee well beyond the time of implantation. For example, the additional reservoir can be periodically filled with a bioactive substance to ensure continued supply of the bioactive substance to the implantation site. The additional reservoir, in this case, may be positioned beneath but adjacent the surface of the skin of the implantee thereby allowing the reservoir to be filled by a syringe and needle assembly that injects the bioactive substance into the additional reservoir.

According to a thirteenth aspect, the present invention is a method of delivering at least one bioactive substance to a desired site of action adjacent a cochleostomy within a patient using a device as defined in the twelfth aspect, the method comprising the steps of:

forming a cochleostomy;
inserting the elongate member through the cochleostomy;
closing the cochleostomy; and
slidably positioning the body of the bioactive substance delivery means adjacent the cochleostomy and allowing said at least one bioactive substance to exit therefrom.

The present invention as defined in each of the above aspects provides a surgeon with an implantable component that can be used with a hearing implant electrode array and that can assist with the delivery of one or more bioactive substances to a position within the cochlea following implantation of the component. The substances that can be delivered by the present device include substances that are adapted to promote healing, substances that prevent bleeding or at least excessive bleeding, and also substances that prevent the growth of tissue, including scar tissue, in the cochlea following implantation. Pharmaceutical compounds such as anti-inflammatories and antibiotics can also be delivered by the present device. It is further envisaged that the bioactive substance may comprise a steroid.

In a particularly preferred embodiment, the bioactive substance comprises a neurotrophic factor including neurotrophins, neuropoietins, insulin-like growth factors, transforming growth factors beta, fibroblast growth factors and other growth factors such as transforming growth factor alpha, platelet-derived growth factor and stem cell factor.

It is also envisaged that substances that assist in reducing the resting potential of the surrounding neurons can also be delivered by the present invention. It should be appreciated that during neural stimulation the neurons propagate an action potential through the response of transmembrane ion channels to local electrical fields. By delivering a substance that elicits a change in the transmembrane potential, the resting neural membrane potential can be moved towards the activation potential resulting in a lowering of the energy required to be delivered to activate the neuron. This also has the potential to reduce the power required by the stimulation device as well as increase the specificity of the electrical stimulation and restore the stochastic response of the neurons.

The device of each aspect may deliver bioactive substances to the preferred site for a particular period following implantation, from a few hours or days to a few weeks or even months.

In a further embodiment of the above aspects, the elongate member of the stimulating device has a plurality of electrodes mounted thereon. The member can have a diameter of about 0.6 mm. The member can also have a first configuration selected to allow said member to be inserted into an implantee's body, such as the cochlea, and a second configuration wherein said elongate member is adapted to apply a preselected tissue stimulation with the electrodes. In a further embodiment, the elongate member can have at least one intermediate configuration between said first and second configurations.

In a still further embodiment of the above aspects, at least a portion of the outer surface of the elongate member can have a coating of lubricious material. In a further embodiment, a substantial portion of the outer surface can have a coating of the lubricious material. In a still further embodiment, the entire outer surface of the elongate member can have a coating of the lubricious material.

The lubricious material preferably becomes lubricious on being brought into contact with a fluid, such as a saline solution. Still further, the coating preferably becomes lubricious on being brought into contact with a body fluid, such as cochlear fluid.

In one embodiment, the lubricious material is selected from the group comprising polyacrylic acid (PAA), polyvinyl alcohol (PVA), polylactic acid (PLA) and polyglycolic acid (PGA). It is envisaged that other similar materials could also be used. It is envisaged that the lubricious material can also be impregnated with the bioactive substance allowing the coating to perform a dual role. The rate of delivery of the bioactive substance can be programmed by design of the coating structure.

In yet another embodiment, the device can include a stiffening element made of a second material relatively stiffer than the resiliently flexible material of the elongate member. The stiffening element can be adapted to bias the elongate member into the first configuration.

In a preferred embodiment, the second configuration of the elongate member is curved. More preferably, the elongate member adopts a spiral configuration when in the second configuration.

The elongate member is preferably preformed from a plastics material with memory and is preformed to the second configuration. In a preferred embodiment, the first configuration is preferably substantially straight. More preferably, the first configuration is straight.

In a preferred embodiment, the elongate member is formed from a suitable biocompatible material. In one embodiment, the material can be a silicone, such as Silastic MDX 4-4210 or other biocompatible silicones. In another embodiment, the elongate member can be formed from a polyurethane or similar material.

In one embodiment, the stiffening element can comprise a metallic stylet, or a stylet-like element formed from any other suitable stiffening material, extending through a lumen in the elongate member. In one embodiment, the wire can be formed from a biocompatible metal, a biocompatible metallic alloy or a biocompatible relatively stiff plastic. In a preferred embodiment, a metal stylet can be formed from platinum.

Once implanted, the electrodes can receive stimulation signals from a stimulator device. The stimulator device is preferably electrically connected to the elongate member by way of the electrical lead. The lead can include the one or more wires extending from each electrode of the array mounted on the elongate member.

In one embodiment, the lead can extend from the elongate member to the stimulator device or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means. In this case, the body of the substance delivery means is preferably positioned around the lead prior to attachment of the lead to the stimulator device.

The stimulator device is preferably positioned within a housing that is implantable within the implantee. In the application of the present invention to hearing implants, the housing for the stimulator device is preferably implantable within the bony well in the bone behind the ear posterior to the mastoid.

When implantable, the housing preferably contains, in addition to the stimulator device, a receiver device. The receiver device is preferably adapted to receive signals from a controller means. The controller means is, in use, preferably mounted external to the body of the implantee such that the signals are transmitted transcutaneously through the implantee.

Signals can preferably travel from the controller means to the receiver device and vice versa. The receiver device can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

In the application of the present invention to hearing implants, the external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear™ implant systems. The encoded sequence is transferred to the implanted receiver/stimulator device using the transmitter and receiver coils. The implanted receiver/stimulator device demodulates the FM signals and allocates the electrical pulses to the appropriate attached electrode by an algorithm which is consistent with the chosen speech coding strategy.

For other applications beyond hearing implants, the external controller can comprise a simple electronic unit capable of being programmed to perform a specific task, such as a predetermined stimulation pattern to a region of the brain or nerves in accordance with a trigger event, such as a sensed body condition or a patient-triggered action.

The external controller further comprises a power supply. The power supply can comprise one or more rechargeable batteries. The transmitter and receiver coils are used to provide power via transcutaneous induction to the implanted receiver/stimulator device and the electrode array.

BRIEF DESCRIPTION OF THE DRAWINGS

By way of example only, a preferred embodiment of the invention is now described with reference to the accompanying drawings, in which:

FIG. 10a is a simplified enlarged view of one embodiment of a prior art electrode assembly;

FIG. 10b is a cross-sectional view of the device of FIG. 10a;

FIG. 11 is a simplified view of an electrode assembly according to another aspect of the present invention;

FIGS. 11a-11c are cross-sectional views of another embodiment of an electrode assembly according to this further aspect of the present invention;

FIG. 19 is a simplified cross-sectional view of one embodiment of an electrode assembly according to another further aspect of the present invention;

FIG. 19a is a cross-sectional view of the device of FIG. 19 through line AA;

FIG. 19b is a cross-sectional view of the device of FIG. 19 through line BB;

FIG. 20 is simplified cross-sectional view of another embodiment of a device according to this further aspect of the present invention;

FIG. 20a is a cross-sectional view of the device of FIG. 20 through line AA; and FIG. 20b is a cross-sectional view of the device of FIG. 20 through line BB.

PREFERRED MODE OF CARRYING OUT THE INVENTION

Figure 1:
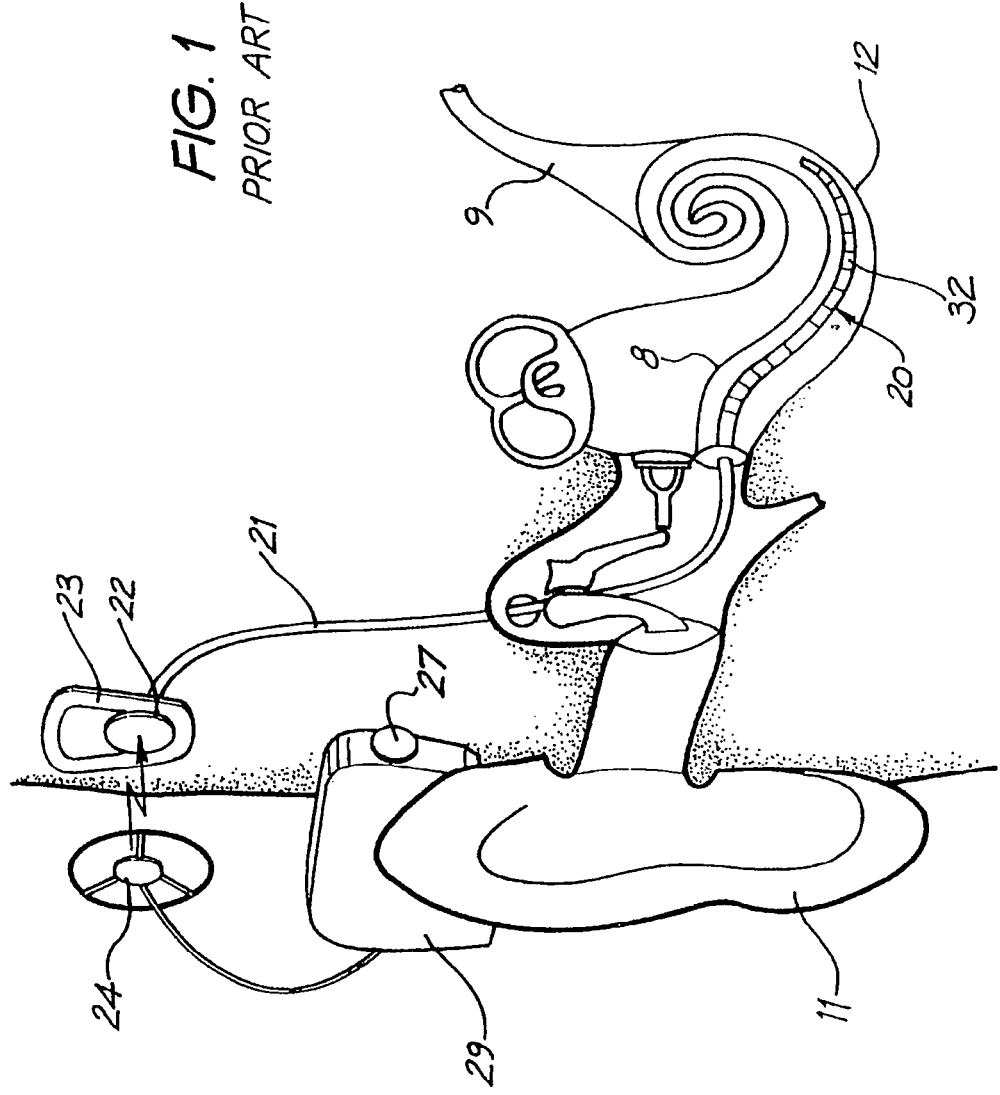
FIG. 1 is a pictorial representation of a prior art hearing implant system.

Before describing the features of the present invention, it is appropriate to briefly describe the construction of one type of known hearing implant system with reference to FIG. 1.

Known hearing implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via a radio frequency (RF) link.

The implanted component includes a receiver coil 23 for receiving power and data from the transmitter coil 24. A lead 21 extends from the implanted receiver and stimulator unit 22 to the cochlea 12 and terminates in an electrode array 20 that is passed through a cochleostomy and into the cochlea 12. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930, the contents of which are incorporated herein by reference.

The array 20 typically comprises an elongate electrode carrier member having a plurality of electrodes mounted thereon. The elongate member is also typically preformed from a resiliently flexible silicone with memory and can be preformed to a curved configuration suitable for insertion in the scala tympani of a human cochlea 12. While an assembly that normally adopts a curved configuration when in a relaxed condition is typically preferred, it will be appreciated that the present invention also could be utilised with respect to assemblies that are normally straight when in a relaxed condition.

Still further, the array 20 typically has a lumen that, prior to insertion of the assembly 20 into the cochlea 12, can receive a substantially straight platinum stylet. Such a stylet typically has a stiffness that is sufficient to retain the silicone elongate member in a straight configuration.

As depicted, the electrode assembly 20 has an electrical lead 21 extending back to a receiver/stimulator unit 22. In considering this invention, it is to be understood that each electrode may have one or more wires electrically connected thereto and extending from each respective electrode 32 back through the lead 21 to the receiver/stimulator unit 22.

Various examples of elongate members according to one aspect of the present invention are depicted in FIGS. 2 to 6b. Where electrodes are depicted in these drawings, it is to be understood that the electrodes are not necessarily shown to scale. A larger number of electrodes than that depicted can also be envisaged.

Figure 2:
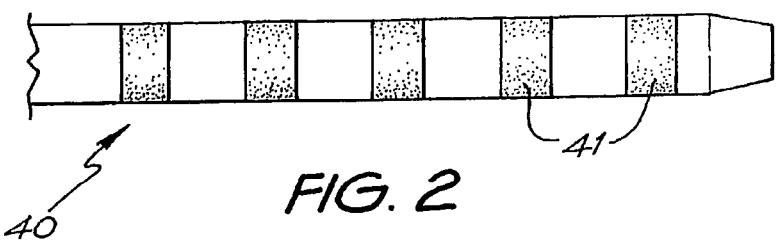
FIG. 2 is a simplified view of one embodiment of an elongate member according to one aspect of the present invention.

FIG. 2 depicts an elongate member 40 having a plurality of electrodes 41 which are formed from a biocompatible porous platinum material. In the depicted embodiment, each of the electrodes 41 are formed from this material and each adapted to deliver electrical stimulation to the cochlea following implantation. It will be appreciated that in another embodiment, only some of the electrodes 41 may be formed from the porous platinum material, with some of the electrodes being formed from a suitable relatively non-porous metallic material, such as platinum as traditionally used in cochlear™ implant electrode arrays. In this embodiment, the electrodes 41 have a bioactive substance disposed within the pores of the platinum material that is able to migrate from the electrodes 41 following implantation of the member 40.

Figure 3:
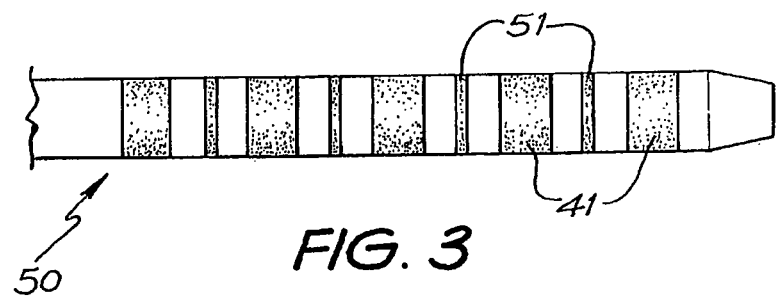
FIG. 3 is a simplified view of another embodiment of an elongate member according to the present invention.

FIG. 3 depicts another embodiment of an elongate member 50 again having a plurality of electrodes 41 which are formed from a biocompatible porous platinum material. In this embodiment, however, the elongate member is provided with a further set of porous platinum rings 51 that are mounted to the member. As depicted, the rings 51 can be disposed between the electrodes 41 mounted on the member. Other locations for the rings can be envisaged. In this embodiment, the rings 51, unlike the electrodes 41, are not adapted to deliver electrical stimulation to the auditory system 12, rather, the electrodes are electrically active but are adapted to create an electrical field to release a drug from the member. If they are electrically active then they can be considered to be electrically stimulating the cochlea but not necessarily delivering auditory stimuli thereto. Like the electrodes 41, the depicted rings 51 have a bioactive substance disposed within the pores of the platinum material that is able to migrate from the rings 51 following implantation of the member 50. In a further example, rings 51 may not deliver electrical stimulation to the auditory system immediately after implantation and their role is limited to release of drugs. Once the supply of drugs has been exhausted, the rings 51 revert to delivering electrical stimulation to the auditory system.

The electrical field required for the release of drugs may be created by stimulation in monopolar, bipolar, tripolar, etc mode.

In a further example, the stimulating electrodes are different from the drug delivering electrodes in either shape and/or in electrical connection.

While FIG. 3 depicts the rings 51 mounted on a member in conjunction with porous platinum electrodes 41, the rings could instead be mounted on an elongate member where some or all of the electrodes are formed from a relatively non-porous platinum as is traditionally used in hearing implant electrode arrays.

Figure 4:
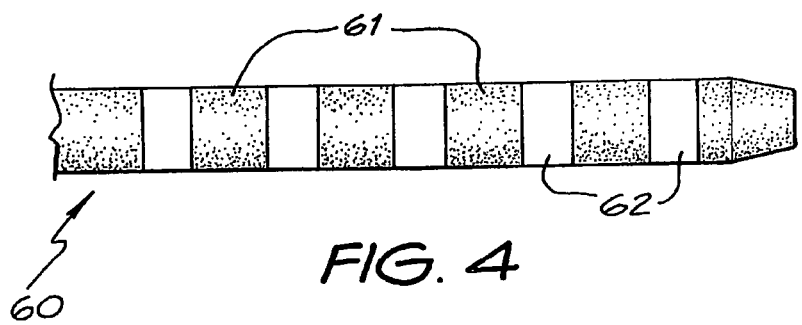
FIG. 4 is a simplified view of still another embodiment of an elongate member according to the present invention.
Figure 5A:
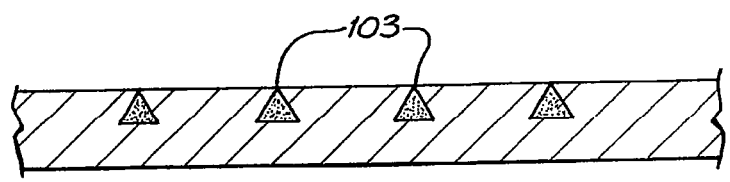
FIGS. 5a and 5b are simplified views of yet another embodiment of an elongate member according to the present invention.
Figure 5B:
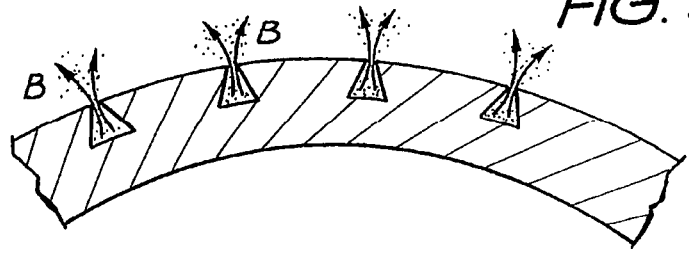

FIG. 4 depicts a still further embodiment of an elongate member 60 in which the material forming the body 61 of the member to which the electrodes 62 are mounted is formed of porous material, such as a porous silicone. The pores of the body 61 have a bioactive substance disposed therein that is able to migrate from the body 61 following implantation of the member 60.

While the depicted electrodes 62 are traditional relatively non-porous electrodes, it will be appreciated that one, some or all of the electrodes 62 could be formed from a porous material, such as a porous platinum.

FIG. 4 also depicts the entire body 61 as being formed from a porous material. In another embodiment, it will be appreciated that only one or more portions of the body 61 could be formed of such a material.

Where the body 61 is comprised of more than one portion, each of the portions can comprise the same material as the remainder of the elongate member but having a plurality of pores disposed therethrough. In one embodiment, the porous portions can comprise the same material as the remainder of the elongate member but which has undergone a processing step to render the portions foraminous.

In another embodiment, the porous portions of the body 61 can be formed from a different material to that of the remainder of the elongate member.

Figure 6A:
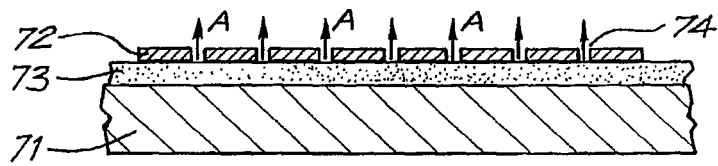
FIGS. 6a and 6b are simplified views of yet still another embodiment of an elongate member according to the present invention.
Figure 6B:
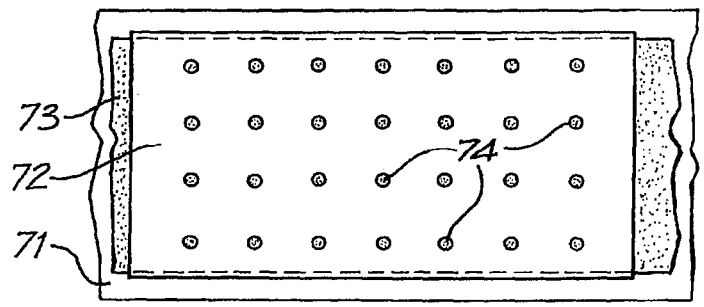

FIGS. 6a and 6b depict a surface of an elongate member 71 that is surrounded by a sheath 72 fabricated from a porous material. As depicted, a quantity of bioactive substance 73 can be disposed beneath the sheath 72 and is free to migrate through the pores 74 in the sheath 72 in the direction of arrows A. In this embodiment, it will be appreciated that the elongate member 71 could have one or more of the features of the other elongate members described herein including those depicted in FIGS. 2-4.

Figure 8:
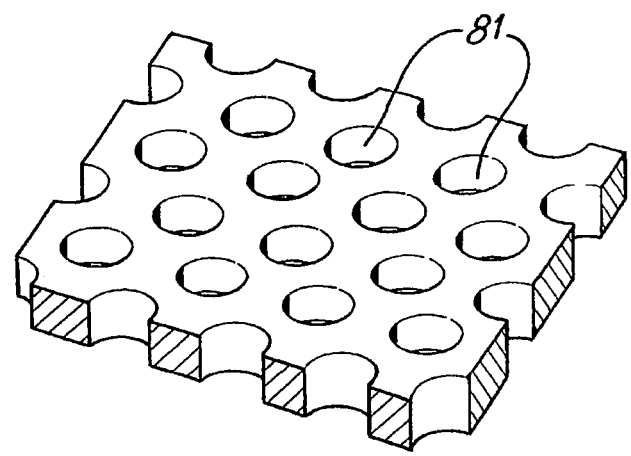
FIG. 8 depicts one type of porous structure for use in one aspect of the present invention.

In each of the embodiments, each pore 81 of the porous material can be an individual pore within the portion, making no interconnection with another pore in the portion such as is depicted in FIG. 8. In FIG. 8, each of the pores 81 are aligned and equally spaced with respect to each other.

Figure 9:
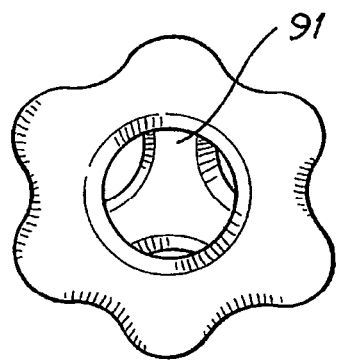
FIG. 9 depicts another type of porous structure for use in the present invention.

As depicted in FIG. 9, the porosity can be in essence in three dimensions with some or all of the pores 91 in a porous portion being interconnected in some way.

In some or each of the porous portions, at least some of the pores or each pore of the porous portion can be at least substantially uniform in cross-sectional shape relative to each other. In another embodiment, the pores can vary in cross-sectional shape from one to at least some of the others.

In some or each of the porous portions, at least some of the pores or each pore of the porous portion can be substantially uniform in diameter. In another embodiment, the pores can vary in diameter from one to at least some of the others.

In some or each of the porous portions, at least some of the pores or each pore of the porous portion can be of a substantially constant diameter along its length. In another embodiment, at least some of the pores or each pore can vary in diameter along its length.

In some or each of the porous portions, at least some of the pores or each pore of the porous portion can have a substantially uniform cross-sectional shape along its length. In another embodiment, at least some of the pores or each pore can vary in cross-sectional shape along its length.

In some or each of the porous portions, at least some of the pores or each pore of the porous portion can be of a substantially constant length. In another embodiment, at least some of the pores or each pore can vary in length relative to at least some of the others in that portion. In one embodiment, at least some of the pores can have relatively extended lengths compared to other pores in that portion.

Figure 7A:
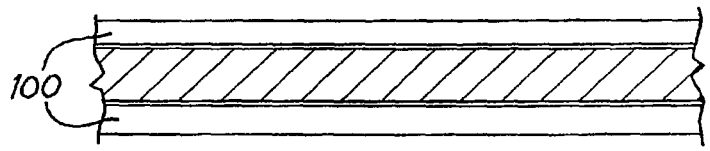
FIGS. 7a, 7b and 7c are views of different types of pores according to the present invention.
Figure 7B:
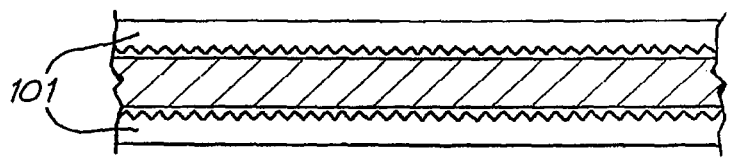
Figure 7C:
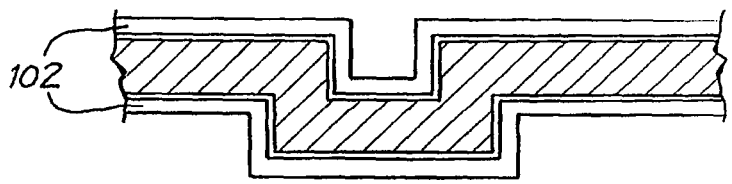

In some or each of the porous portions, at least some of the pores or each pores of the porous portion can be at least substantially linear, such as respective pores 100 and 101 depicted in FIGS. 7a and 7b. In another embodiment, at least some of the pores or each pores of the porous portion can be non-linear such as pore 102 depicted in FIG. 7c.

In some or each of the porous portions, at least some of the porous portions or each porous portion can have substantially the same of pores per unit area. In another embodiment, at least some of the porous portions or each porous portion can have differing number of pores per unit area relative to that of at least some of the other porous portions.

In some or each of the porous portions, at least some of the pores in one, some or each of the porous portions can have relatively smooth internal walls, such as pore 100 depicted in FIG. 7a. In another embodiment, at least some of the pores in one, some or each of the porous portions can have rippled internal walls, such as pore 101 depicted in FIG. 7b. The ripples can have a suitably small dimension to preferably at least substantially prevent wetting of the cavities thereby minimising friction between the bioactive substance and the walls.

The nature of the porosity between separate porous portions of the device may be the same or vary from one to at least some or all of the other portions. For example, the dimension of the pores of a porous portion relatively close to the distal end of the elongate member may be different to the dimensions of the pores of a porous portion that is relatively close to the proximal end of the elongate member. In this embodiment, the portion relatively closer to the distal end can have pores having a diameter and/or length greater than the pores of the porous portion relatively closer to the proximal end of the elongate member. In another embodiment, the relative porosity of different portions can be essentially random.

In some or each of the porous portions, at least some of the pores of the porous portion can be preferably adapted to be at least substantially closed when the elongate member is at least substantially straight thereby preventing migration of any bioactive substance held within said at least some pores from these pores. See, for example FIG. 5a which depicts pores 103 as adopting a closed configuration when the elongate member is straight. On adopting a curved configuration, the pores 103 are adapted to at least partially open allowing migration of the bioactive substance therefrom, as represented by arrows B.

In this invention, the bioactive substances can be free to simply migrate from the pores of the porous portions following implantation of the device. In another embodiment, the bioactive substance can be dispersed in an ionic fluid that is preferably caused to migrate from the pores on application of a suitable electrical field thereto. In another embodiment, the bioactive substance can be dispersed in an ionic solution that is allowed to diffuse from the pores and/or be expelled therefrom under application of a suitable electric field.

In one embodiment, the bioactive substance can be dispersed in a suitable fluid. In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation.

In the present invention, the at least one bioactive substance can be delivered to a desired site of action within a cochlea using a device as described herein. The method preferably comprises the steps of:

forming a cochleostomy;

inserting the elongate member as described herein through the cochleostomy;

allowing or causing the bioactive substance to migrate from the elongate member into the cochlea.

In this method, the pores of the device are at least partially filled by dipping the elongate member in the bioactive substance for a suitable time period. This step can be performed immediately after manufacture of the elongate member. In another embodiment, the step can be performed just prior to implantation of the member into the implantee.

FIG. 10a shows a prior art array 120 comprising an elongate electrode carrier member 131 having a plurality of electrodes 132 mounted thereon.

As depicted in FIG. 10b, the array 120 typically has a lumen 134 that, prior to insertion of the assembly 120 into the cochlea, can receive a substantially straight platinum stylet. Such a stylet typically has a stiffness that is sufficient to retain the silicone elongate member 131 in a straight configuration.

A resiliently flexible elongate member according to a further aspect of the present invention is depicted generally as 140 in FIGS. 11 and 11a. The member 140 has a plurality of electrodes 132 mounted thereon for delivering electrical stimulation to the cochlea.

Within the member 140 is at least a partially encapsulated member 141 of biocompatible material that has been impregnated with at least one bioactive substance. In this embodiment depicted in FIG. 11, the member extends for at least a majority of the length of the elongate member and is of a substantially constant diameter along its length.

As can be determined from a comparison of FIGS. 11a and 11b, the cross-sectional shape of the member 141 can vary from one array to the next. Also, in another embodiment as depicted in FIG. 11c, the member 142 can be inserted through the lumen 134 used by the stylet during implantation of the array in the cochlea of an implantee.

Figure 12:
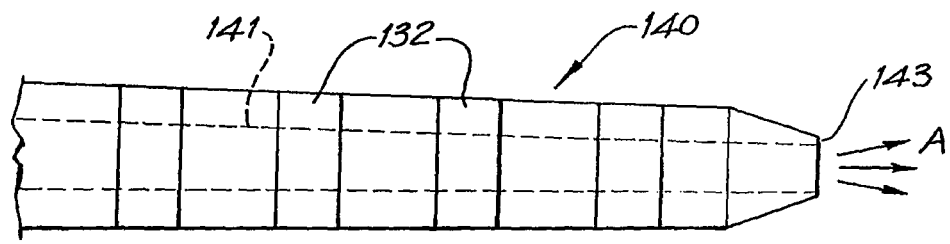
FIG. 12 is a simplified view of another embodiment of an electrode assembly according to the further aspect of the present invention.
Figure 13:
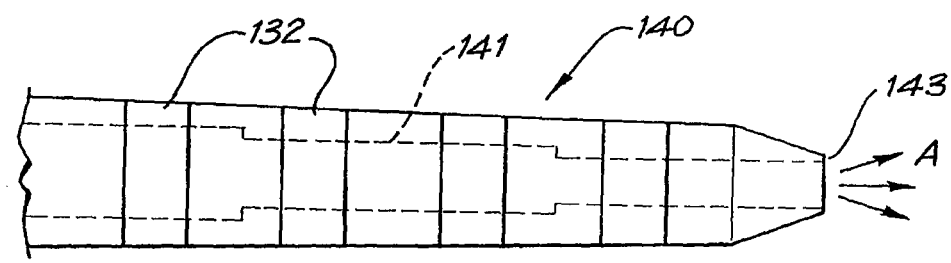
FIG. 13 is a simplified view of a still further embodiment of an electrode assembly according to this aspect of the present invention.

As depicted in FIGS. 12 and 13, the member 141 can vary in diameter along its length. For example, as depicted in FIG. 12, the diameter of the member 141 can gradually taper from the proximal end towards the distal end of the elongate member 140. In FIG. 13, the diameter decreases in a step-wise fashion from the proximal end towards the distal end.

Figure 14:
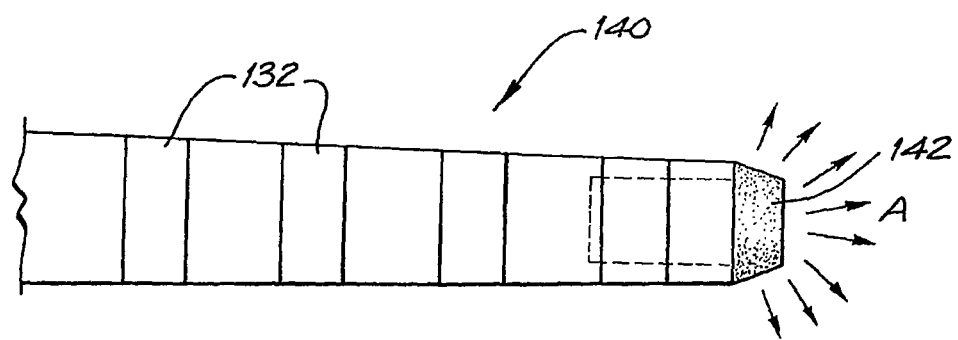
FIG. 14 is a simplified view of a still further embodiment of an electrode assembly according to this aspect of the present invention.

FIG. 14 depicts a still further embodiment where an impregnated plug-like member 142 extends into the elongate member 140 from the distal end thereof.

One or more openings can be provided in the elongate member 140 to allow bioactive substances in the member 141 or 142 to diffuse from the member and exit the elongate member. Openings can be provided at various locations along the member, including the distal end 143 of the elongate member. Arrows A depict possible locations of diffused bioactive substance into the cochlea.

There can instead or also be one or more openings at a location spaced from the distal end 143. Where there is more than opening, the openings can be regularly or irregularly spaced along the elongate member.

As is depicted in FIGS. 15 to 18, the elongate member can have impregnated members disposed in the outer face of the elongate member.

Figure 16A:
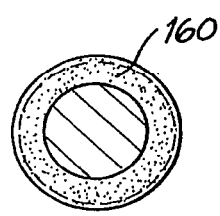
FIGS. 16a-16c are cross-sectional views of an electrode assembly according to this aspect of the present invention.
Figure 16B:
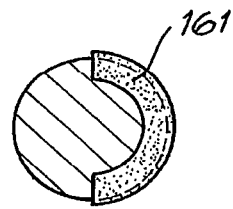
Figure 16C:
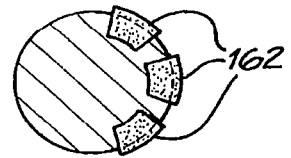

As depicted in FIGS. 16a, 16b and 16c, the impregnated members can comprise a ring member 160 (FIG. 16a) or a half-ring member 161 (FIG. 16b) disposed in the outer face of the elongate member. In another embodiment, the impregnated member can comprise a number of portions 162 that are disposed along the locus of a ring formed in the outer surface of the elongate member (see FIG. 16c).

Figure 15:
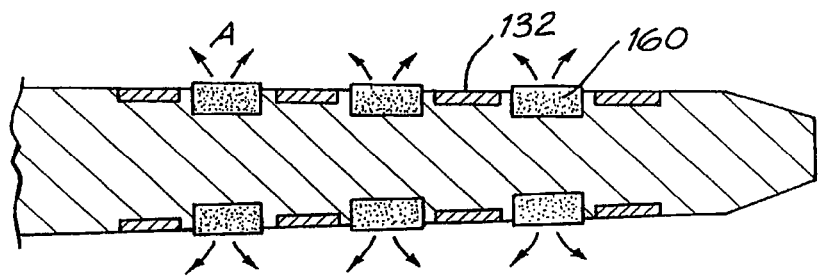
FIG. 15 is a simplified view of a still further embodiment of an electrode assembly according to this aspect of the present invention.

FIG. 15 depicts how a plurality of rings 160 can be disposed between the electrodes 132 of the array. It will be appreciated that the rings 160 of FIG. 15 could be replaced in one, some, or all instances, by half-rings 161 or ring portions 162. In the depicted embodiment, the ring members 160 stand just proud of the outer surface of the elongate member. It will be appreciated that one or more of the ring members etc could be at least substantially flush with the outer surface of the elongate member or be recessed in the elongate member.

Figure 17:
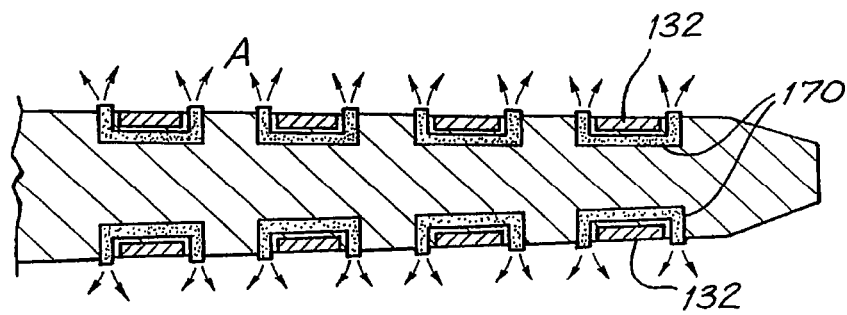
FIG. 17 is a simplified view of a still further embodiment of an electrode assembly according to this further aspect of the present invention.

As depicted in FIG. 17, impregnated portions 170 can be disposed around the electrodes 132 mounted in the elongate member. Where the electrode comprises a ring or ring portion, the portion can comprise an annular or part-annular member that surrounds the electrode 132.

Figure 18:
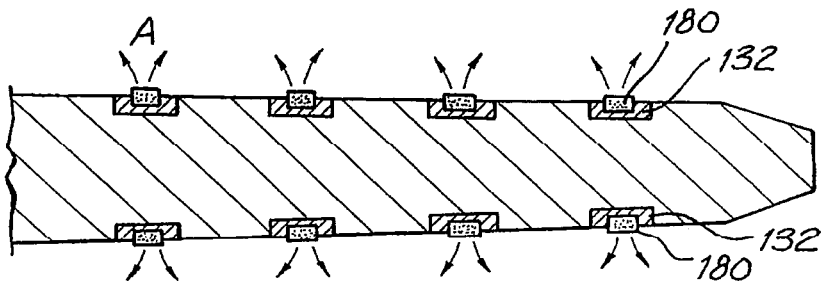
FIG. 18 is a simplified view of a further embodiment of an electrode assembly according to this aspect of the present invention.

As depicted in FIG. 18, the electrode 132 can be disposed around an impregnated portion 180 of biocompatible polymeric material.

One embodiment of a further aspect of a hearing implant electrode assembly incorporating a system for delivery of bioactive substances is depicted generally as 230 in FIG. 19.

The assembly 230 includes an elongate member 231 that has a distal end 233 that is firstly inserted into the cochlea upon insertion of the assembly 230.

As depicted in FIG. 19, a collar 240 is slidably disposed around the lead 21. The collar 240 is part of a system for delivering one or more pharmaceutical or bioactive substances to a location just external the cochleostomy of the cochlea.

In FIG. 19, the collar 240 can be moved along the lead 21 towards the distal end 233 of the array member until it reaches a stop member that prevents further slidable movement of the collar in that direction.

The collar 240 has a stepped outer surface 241 defined by two cylindrical portions 242 and 243. In the depicted embodiment, the collar 240 is symmetrical about its longitudinal axis and has parallel proximal and distal ends 244,245.

The outlet 246 of the collar 240 is positioned in the distal end 245 of the collar 240. In the depicted embodiment, the collar 240 further has an inlet 250 in the proximal end 244 of the collar 240. The inlet and outlet are in communication, such as fluid communication, with each other.

As depicted in FIG. 19, the outlet 246 of the collar 240 comprises an annular opening in the distal end 245 of the collar. The chamber 247 within the collar extends back into the collar 240 from the outlet 246. As the depicted outlet 246 is an annular opening, the chamber 247 is also annular in form and so comprises a cylindrical chamber having an outer and inner surface and extending back into the collar from the outlet 246. It will be appreciated, however, that the outlet and chamber need not be annular to fall within the scope of the present application.

The annular chamber 247 has a frusto-conical region 248 where the outer and inner walls of the chamber 247 move away from the longitudinal axis of the collar 240, and a further cylindrical region 249 distal the outlet. In this embodiment, the inlet 250 comprises a pipe extending from the proximal end 244 of the collar into the chamber 247. The inlet 250 is adjacent the outer wall 241 of the collar 240.

A different construction of a collar is generally depicted as 260 in FIGS. 20, 20a and 20b. As depicted, the chamber can instead comprise a non-linear pipe 261 extending from the proximal end 244 to the distal end 245 of the collar 260. The inlet 250 is positioned at least partially further outwardly from the longitudinal axis of the collar 260 body relative to the outlet 246.

The distal end 233 of the elongate member is preferably firstly inserted into the cochleostomy of the implantee during placement of the implant.

The chamber in the collar acts as a reservoir for a bioactive substance. This bioactive substance in the chamber diffuses from the chamber into the implantee through a semi-permeable membrane 270 in the outlet 246. The membrane 270 allows the bioactive substance to leach from the chamber during and/or following implantation to the desired site of action for the bioactive substance.

Where the bioactive substance is carried in or comprises a fluid, the semi-permeable membrane 270 allows the fluid to leach or diffuse therethrough.

The membrane 270 can act as a valve means that allows fluid to exit the chamber but prevents, or at least substantially prevents, fluid flow from external the chamber back into the chamber within the body.

A catheter 280 can extend from the inlet 250 to an additional reservoir for a bioactive substance. A pump, such as an osmotic pump, can transfer the bioactive substance from the additional reservoir into the chamber of the body for subsequent delivery to the appropriate site of action.

It is also envisaged that the bioactive substance can be captured in the form of a solid or semi-solid pellet. In one embodiment, the pellet can be formed by impregnating the bioactive substance in a ceramic or a polymer pellet that has a predetermined rate of release of the bioactive substance. This solid pellet can then be stored in the chamber or in an external reservoir connectable to the chamber.

The provision of a system for delivering a pharmaceutical substance in the cochlea that promotes healing and/or more efficient neural stimulation while preventing the formation of substantial scar tissue in the cochlea, enhances the likelihood of successful long-term placement of the elongate member in the cochlea and subsequent successful use of the hearing implant by the implantee.

While the preferred embodiment of the invention has been described in conjunction with a hearing implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An implantable tissue stimulating device comprising:
   an electrode assembly comprising a lead and an elongate member having its proximal end contiguous with a distal end of the lead, and having one or more electrodes disposed on or in the elongate member; and
   a slider means for delivery of a bioactive substance slidably mounted on the lead such the lead extends through the slider means, the slider means configured to receive a bioactive substance and deliver the bioactive substance to a target site in the recipient.

2. The device of claim 1, further comprising:
   a stop member, disposed on the electrode assembly, configured to prevent the slider means from sliding beyond the stop member toward a distal end of the elongate member.

3. The device of claim 1, wherein a portion of the lead is configured to be implanted in a middle ear of the recipient, and wherein the slider means is dimensioned to slide along a portion of the lead implanted in the middle ear.

4. The device of claim 1, wherein the slider means has a plurality of different diameters along the length of the slider means.

5. The cochlear implant of claim 1, wherein the slider means includes a chamber configured to receive a bioactive substance and configured to retain the bioactive substance therein for a period of time.

6. The cochlear implant of claim 5, wherein the chamber is annular and surrounds a lumen of the slider means through which the electrical lead passes.

7. The device of claim 5, wherein the slider means further comprises:
   an outlet in fluid communication with the chamber; and
   a semi-permeable membrane disposed in the outlet and configured to leach the bioactive substance from the chamber to the target site.

8. The device of claim 5, wherein the slider means further comprises:
   an inlet in fluid communication with the chamber.

9. The cochlear implant of claim 8, wherein the slider means further comprises:
   an outlet in fluid communication with the chamber,
   wherein the chamber is configured to pass the bioactive substance from the inlet to the outlet.

10. The cochlear implant of claim 8, wherein the inlet is disposed in a proximal end of the slider means, and the outlet is disposed in a distal end of the slider means.

11. The cochlear implant of claim 10, wherein the chamber is a pipe extending through the slider means from the inlet to the outlet.

12. The device of claim 1, wherein:
the device is a cochlear implant.

13. A cochlear implant comprising:
a stimulator unit configured to generate electrical stimulation signals;
an electrode assembly comprising a lead extending from the stimulator unit, and a contiguous elongate member implantable in a recipient's cochlea;
one or more electrodes disposed on or in the elongate member each configured to deliver the electrical stimulation signals to the cochlea; and
an annular collar slidably mounted around the lead such that the lead extends through a lumen in the collar, the collar having a non-porous cavity therein configured to receive a bioactive substance and an outlet located on an exterior face of the collar through which the bioactive substance can pass from the cavity to a target site in the recipient,
wherein the outlet faces the electrode assembly and forms a boundary of the cavity.

\* \* \* \* \*